US005399730A

United States Patent [19]

[11] Patent Number: 5,399,730

Koupchinov et al.

[45] Date of Patent: Mar. 21, 1995

[54] METHOD OF OBTAINING AN PURIFIED WOOL FAT AND USE AS AN ADDITIVE TO LUBRICANTS

[75] Inventors: Boris I. Koupchinov; Viktor P. Parkalov; Vladimir G. Rodnenkov; Sergey F. Ermakov, all of Gomel; Vitaly G. Tischenco, Charkov; Lenoid A. Sarkisov, Charkov; Feliks E. Gulijaev, Charkov, all of U.S.S.R.; Vladimir N. Kestelman, Pennsauken, N.J.; Anatoly I. Sviridenok, Gomel, U.S.S.R.

[73] Assignee: Development Products, Inc., Radnor, Pa.

[21] Appl. No.: 739,762

[22] Filed: Aug. 1, 1991

[51] Int. Cl.$^6$ ........................ C07C 51/02; C07C 51/42

[52] U.S. Cl. .................................... 554/167; 554/170; 554/175; 554/206; 554/207; 554/208; 554/174

[58] Field of Search ..................... 554/8, 174, 170, 30, 554/167, 175, 206, 207, 208

[56] References Cited

U.S. PATENT DOCUMENTS 3,835,169 9/1974 Kraft et al. .......................... 554/170

OTHER PUBLICATIONS

Hasegawa et al, Chemical Abstracts, vol. 112, #14, 1989, 124947q.

Koresawa et al, Chemical Abstracts, vol. 88, #2, 1978, 154747c.

*Primary Examiner*—José G. Dees
*Assistant Examiner*—Deborah D. Carr
*Attorney, Agent, or Firm*—Simpson & Simpson

[57] ABSTRACT

This invention relates to a purified wool fat essentially free from low molecular weight volatile acids, water soluble aliphatic alcohols and water. This purified wool fat is produced by effecting the esterification of free alcohols and fatty acid contained in the wool fat followed by solvent extraction and chromatographical purification of the extracted solvent. The purified wool fat can be used as a lubricant enhancer in lubricating oils.

2 Claims, No Drawings

METHOD OF OBTAINING AN PURIFIED WOOL FAT AND USE AS AN ADDITIVE TO LUBRICANTS

BACKGROUND OF THE INVENTION

This invention relates to additives for lubricating oils and to the methods of obtaining and using them, particularly in the machine building and instrument engineering industries.

Known in the art are additives for oils consisting of the esters of unsaturated $C_{10}$–$C_{20}$ fatty acids and of $C_1$–$C_3$ monohydric alcohols which have been subjected to interaction with sulfur monochloride at a temperature of 20 to 80 degrees; the amount of sulfur is 10 to 40 percent by weight in relation to fatty acid [GDR Pat. No. 293,365, 1971]. However, the oils containing this additive are intended only for use in plastic metal working and cannot be used for lubricating friction assemblies since they cause a heavy corrosion of metals due to the presence of sulfur.

Known in the art are lubricants where esters of cholesterol and fatty acids are used to enhance the service properties [USSR inventors Certificate No. 601,304, 1978]. Such methods of enhancing the lubricating properties of oils has not found a wide use because of a high cost and deficiency of cholesterol required for the synthesis of esters since it is obtained from the cerebrum and spinal cord of animals.

There is also known the method of obtaining additives for lubricants in which wool fat is purified by alkalies to remove acids, then whitened with oxidizers and adsorbents so that a purified wool fat (lanolin) is obtained [P. I. Belkevitch, et al, "Wax and its technical analog," Minsk, "Science and Engineering," 1980, p.p. 14–16.]Introduction of this additive into a lubricant results in the reduction of the frictional force. However, this additive does not possess high anti-corrosive properties and can be used at insignificant loads only.

It is a primary object of this invention to provide an oil additive that will reduce the friction coefficient and increase the load capability and anti-corrosion properties of lubricating oils.

The additive of the present invention is obtained and the objects are achieved by subjecting untreated wool fat to heat in an inert atmosphere at a temperature of 150° to 200° C. The resulting product is treated for 8 to 10 hours with a nonaqueous polar solvent at a temperature of at least 80°, e.g. 80° to 100° C., until it is essentially completely dissolved. The solution/mixture is then cooled to a temperature in the range of minus 20 to minus 30° Centigrade; precipitated sediment is separated and dissolved in nonpolar organic solvent at room temperature. This second solution is flushed with water, the water is separated, and the solution is dehydrated by use of silica gel and subjected to chromatographic purification with the subsequent removal of the solvent to produce the oil additive. To increase the yield of the additive, the heat treatment of wool fat in the inert atmosphere is effected in the presence of 0.2 to 1.0 parts by mass of fatty acid to 3 parts by mass of the wool fat.

The wool fat is mainly obtained as a by-product during the pretreatment of wool (by washing it with water in centrifuges). The untreated wool fat separated out of the flushing water contains, apart from the wax, free fatty acids, glycerins, albumins, mucuses, dyes, mineral admixtures, et cetera. The chemical composition of the wool fat is very multiplex and is not completely determined. Its basic components are subdivided into the mixture of esters of fatty acids and the higher aliphatic and cyclic (mainly, the representatives of sterols, such as cholesterol, isocholesterol, oxicholesterol, metacholesterol, et cetera) alcohols and the mixture of the said chemically pure (nonesterificated) alcohols with free fatty acids and with some amount of low molecular acids. Wool fat has the following physical and chemical properties:

| | |
|---|---|
| density at 15 degrees C., Kg/m$^3$ | 932 to 945 |
| temperature, degrees C. | |
| of melting | 31 to 43 |
| of solidification | 30 to 40 |
| saponification number | 77 to 130 |
| iodine number | 15 to 29 |

The presence of free low-molecular and the higher aliphatic acids in the wool fat, upon long-term contact with metals, causes corrosion. The corrosive effect of the additive on the basis of wool fat is also aggravated by the fact that it possesses high hygroscopicity and is capable of absorbing up to 300% of water since, apart from the water-soluble low-molecular weight volatile acids, it also contains the lower aliphatic alcohols which are also water-soluble and capable of absorbing water from the air.

It is common knowledge that the presence of water brings about the reduction of carrying capability of the lubrication layers and, as a consequence, the reduction of the anti-abrasive and anti-wear properties.

To eliminate the said disadvantages, the method envisages the additional treatment of the wool fat ensuring the formation of water-insoluble esters and the removing from the wool fat those compounds of the mixture which result in the above-mentioned negative properties of the lubricant. Besides, this method makes it possible to increase the yield of the product as compared with the case of a simple removal of unwanted components from the wool fat composition. Thus, the inventive process includes the esterification of free alcohols and free fatty acids present in the composition of wool fat by way of its heat treatment at a temperature of 150° to 200° C. in the presence of additionally introduced fatty acid or mixture of fatty acids. In the process, apart from the water-soluble lower alcohols, subjected to esterification are also monohydric aromatic alcohols-sterols. To prevent the products from being oxidized in the process of synthesis, nitrogen is continuously sparged through the reaction mixture. The thus obtained esters of fatty acids possess very high lubrication properties. To remove the nonreacted components of wool fat (extra fatty acids, mineral admixtures, dyes), the product obtained as a result of esterification is then subjected to further treatment. First, it is dissolved in polar nonaqueous solvent at a temperature of 80° to 200° C., which ensures a complete dissolving of all the mixture components (at room temperature, the product is dissolved incompletely). If use is made of nonpolar organic solvent at this stage of the process, all the mixture components will be dissolved in this solvent including the esters of sterols and higher fatty acids. In this case, further separation of the components will become impossible. After the product is carefully stirred in the polar solvent, the solution is subjected to a deep cooling down to a temperature of minus 20° to minus 30° C. In the process, the esters (of sterols and lower alcohols) drop out as a precipitate (at room temperature and at a temperature exceeding this temperature, a considerable portion of esters remains in the solution) which is separated and dissolved in the nonpolar organic solvent at room temperature and the obtained solution is flushed with ice. As a result, the polar organic solvent and any mineral salts are completely removed (dissolved in water). After allowing the mixture to settle, the aqueous portion of the solution is removed by decantation and the remaining portion (the solution in nonpolar organic solvent) is treated with the use of granulated silica gel for complete dehydration and subjected to chromatographic purification. After the solution is passed through the chromatographic column filled with, e.g., silochrome or aluminum oxide, it is purified from dyes and other by-products. After the solvent is removed, for example, by distillation, there is obtained the additive consisting of the mixture of esters and higher molecular weight alcohols and fatty acids. The additive obtained using this method is essentially a viscous mass of yellowish-grey color having a density of 0.750 to 0.900 g./cm.$^3$. At a temperature of 45°±5° C., the product gets clarified. For implementation of this method, use is made of the following materials: wool fat, dimethylformamide, acetone, hexane, gasoline, acetonitrile, stearic acid, olein (a mixture of oleic, linolenic and palmitic acids), aluminum oxide, silochrome, petrolatum, and industrial-grade oil.

Technological parameters for implementation of the present process are presented in Table 1.

TABLE 1

| Example No. | Wool Fat-to-Fatty Acid Mass Ratio | Wool Fat Heat Treatment Temperature, °C. | Heat-Treatment Time, Hours | Polar Solvent Cooling Temperature, °C. | Product Yield % of Starting Material |
|---|---|---|---|---|---|
| 1 | 100% Wool Fat | 140 | 7 | +20 | 71.0 |
| 2 | 3:0.1 Stearic Acid | 140 | 7 | −10 | 72.5 |
| 3 | 3:0.1 Oleic Acid | 150 | 7 | −20 | 73.2 |
| 4 | 3:0.2 Stearic Acid | 150 | 8 | −20 | 85.0 |
| 5 | 3:0.5 Oleic Acid | 170 | 9 | −25 | 87.3 |
| 6 | 3:1.0 Stearic Acid | 190 | 10 | −25 | 88.5 |
| 7 | 3:1.0 Oleic Acid | 200 | 9 | −30 | 89.0 |
| 8 | 3:1.5 Stearic Acid | 220 | 11 | −40 | 88.8 |
| 9 | 3:1.5 Oleic Acid | 230 | 7 | −40 | 88.4 |
| 10 | 100% Wool Fat | 170 | 9 | −25 | 75.0 |
| 11* | 3:1.0 Oleic Acid | 170 | 9 | −25 | 90.1 |
| 12** | 3:1.0 Oleic Acid | 170 | 9 | −25 | 90.5 |

*When implementing the method, the stage of treating the product with granulated silica gel is absent.
**When implementing the method, the stage of chromatographic purification of the product solution in nonpolar organic solvent is absent.

The obtained samples of additive are introduced in the amount of 1.5% by mass into petrolatum and industrial oil. The friction coefficient is measured with the help of a friction machine according to the "shaft-partial insert" scheme using a steel-bronze friction pair at a slipping rate of 0.5 m/s and at a load of 10 MPa.

The loading capability of the lubricants with additives is measured on a steel-steel pair according to the following scheme: rotary roller with spherical surface-stationary cylindrical roller. The lubricant is fed to the friction zone continuously by immersing a portion of the roller into a bath. The rotational speed of cylindrical roller during test is 500 rpm. The initial roughness degree of the surfaces of rollers is 0.600–0.630μ. The load applied to the friction pair is increased in steps of 0.1 MPa. When the lubrication layer working limit for the load is reached, there occurs scoring of the friction pair, which is accompanied by an abrupt increase of the friction coefficient. Thereafter, the lubricant test was stopped.

The anti-corrosive properties of lubricants with the obtained additives are measured at a temperature of 140° C. by checking the variation of mass of exposed lead plates after 50 hours of tests. The test results of lubricant compositions are presented in Table 2.

TABLE 2

| Lubricant Composition | Tribotechnical Characteristics: Friction Coefficient | Tribotechnical Characteristics: Maximum Working Load of Friction | Anti-corrosive Properties: Loss of Mass of Lead Place g/m$^2$ |
|---|---|---|---|
| Petrolatum + Additive According to Example No.: | | | |
| 1 | 0.017 | 15 | 10.90 |
| 2 | 0.017 | 16 | 11.00 |
| 3 | 0.016 | 16 | 9.55 |
| 4 | 0.010 | 28 | 5.10 |
| 5 | 0.010 | 30 | 4.60 |
| 6 | 0.009 | 30 | 4.95 |
| 7 | 0.008 | 30 | 4.75 |
| 8 | 0.013 | 20 | 8.30 |
| 9 | 0.015 | 19 | 8.90 |
| 10 | 0.011 | 28 | 5.30 |
| 11 | 0.010 | 16 | 6.90 |
| 12 | 0.020 | 14 | 12.50 |
| Industrial Oil + Additive According to Example No.: | | | |
| 1 | 0.016 | 17 | 10.80 |
| 2 | 0.016 | 17 | 10.50 |
| 3 | 0.016 | 17 | 9.80 |
| 4 | 0.009 | 29 | 5.00 |
| 5 | 0.009 | 30 | 4.85 |

TABLE 2-continued

| Lubricant Composition | Tribotechnical Characteristics: Friction Coefficient | Tribotechnical Characteristics: Maximum Working Load of Friction | Anti-corrosive Properties: Loss of Mass of Lead Place g/m$^2$ |
|---|---|---|---|
| 6 | 0.008 | 29 | 4.90 |
| 7 | 0.008 | 30 | 5.00 |
| 8 | 0.012 | 21 | 8.50 |
| 9 | 0.015 | 18 | 8.65 |
| 10 | 0.011 | 27 | 5.35 |
| 11 | 0.010 | 15 | 6.60 |
| 12 | 0.020 | 16 | 12.40 |
| Petrolatum + Additive According to Prior Art Purified Wool Fat Additive | 0.018 | 15 | 8.00 |
| Industrial Oil + Additive According to Prior Art Purified Wool Fat Additive | 0.018 | 16 | 7.90 |

The analysis of the operating characteristics of the lubricant samples shows that the additives obtained under conditions outside the specified ranges of the present invention do not ensure enhancing of the quality of lubricants. So, for example, when introducing the additives according to Examples 1 to 3 into petrolatum or industrial oil, the values of the friction coefficient and loading capability of lubricants are practically at the same level with the parameters of the lubricants containing the prior art wool fat additive, and the anti-corrosive properties of the lubricants are considerably lower. Similarly, although compared to the prior art method the indexes of the friction coefficient and loading capability of lubricants for Examples 8 and 9 are somewhat better, the anti-corrosive properties of these lubricants happen to be even lower as compared with the prior art method.

When implementing the method within the limits of the claimed ranges (Examples 4–7), introduction of the respective additives ensures a reduction of the friction coefficient from 0.018 (for the prior art additive) to 0.008–0.010, an increase of the loading capability of the lubrication layers from 15–16 MPa to 28–30 MPa and an increase of the anti-corrosive properties (with reference to the index showing the reduction of the lead plate mass loss) from 8 g/m$^2$ to 4.60–5.10 g/m$^2$.

When subjecting the wool fat to heat treatment in the presence of 0.2 to 1.0 percent by mass of fatty acid (e.g., stearic acid), the yield of a high quality additive is increased from 75% (Example 10, Table 1) to 85-89% (Examples 4–7). Introduction of fatty acid in an amount greater than 1.0% by mass into wool fat before subjecting it to heat treatment has practically no effect on the yield of additive (Example 8–9) and, consequently, is not useful. The treatment of wool fat without additional introduction of fatty acid (Example 10), provided other conditions of the method are fulfilled, makes it possible to obtain the additive with high service properties. However, in this case, 25% of valuable starting material gets lost.

Excluding of the product dehydration stage with the use of silica gel (Example 11, Table 1) or the chromatographic purification stage (Example 12, Table 1) from the technological process of obtaining the additive results in the reduction of the operating characteristics of lubricants containing the said additives (compositions 11, 12 in Table 2 ).

Thus, the use of this method of obtaining the additive to lubricants brings about the reduction of the friction coefficient 1.8 to 2.3 times, the increase of anti-abrasive properties of the lubricant 1.7 to 1 . 9 times and of anti-corrosive properties, 1.6 to 1.7 times; it also expands the possibilities of reprocessing the raw materials with a high percentage of usage.

The following examples provide a more explicit description of the practice of the invention.

EXAMPLE 13

4 kg. of palmitic acid were added to 12 kg. of wool fat and the mixture was heated to a temperature of 160° C. Then, gaseous nitrogen was fed to the reaction vessel and the synthesis process was performed with the nitrogen continuously passed through and the temperature being equal to 160°–180° C. Within 10 hours, the reaction mixture was cooled down to a temperature of 90°–100° C. and dissolved in 15 liters of dimethyl formamide while stirring for 5 to 10 minutes. The resulting solution was cooled down to a temperature of minus 10°–±5° C. On reaching the desired temperature, precipitation occurred and the precipitate was separated by decantation of the solvent. The obtained precipitate was washed with 10 liters of water at room temperature. Upon settling, the water was decantated and the obtained product was heated for 10 minutes at a temperature of 100° to 115° C. to eliminate the water. This done, the process of obtaining the additive was considered to be over. The product yield was 13.5 kg.

EXAMPLE 14

A mixture of 12 kg. of wool fat and 4 kg. of olein was subjected to heat treatment for 8 hours at a temperature of 200° C. with nitrogen continuously passed through and then the mixture was cooled down to a temperature of 100° C. and dissolved in 15 liters of acetone. Upon a thorough stirring, the solution was cooled down to a temperature of minus 25°±5° C. After the precipitate was formed, the soluble portion was decantated and the precipitate was washed with 10 liters of water. The water was subsequently separated and the solids were dissolved in 15 liters of gasoline at room temperature. The solution was then passed through a filter filled with granulated silica gel followed by chromatographic cleaning with aluminum oxide. Upon distillation of gasoline, the process of obtaining the additive was considered to be over. The product yield was 11 kg.

EXAMPLE 15

12 kg. of wool fat without additional introduction of fatty acid were treated as in Example 14. The product yield was 8 kg.

EXAMPLE 16

2 kg. of olein were added to 12 kg. of wool fat and further treatment was performed as in Example 14. The product yield was 9.2 kg.

EXAMPLE 17

5 kg. of palmitic acid were added to 12 kg. of wool fat. Further treatment was effected as in Example 14, but used as the polar solvent was acetonitrile and as the unpolar solvent (before the chromatographic cleaning), hexane. The product yield was 12.3 kg.

EXAMPLE 18

4 kg. of olein were added to 12 kg. of wool fat and bypassing the heat treatment stage in the inert medium, the mixture was dissolved in 15 liters of dimethylpharmamide at a temperature of 100° C. while stirring for 10 minutes. Further treatment was performed as in Example 14. The product yield was 8.2 kg.

What is claimed is:

1. A method of producing a lubricant enhancer which comprises the steps of:

(a) heating wool fat in an inert atmosphere at a temperature of 150° to 200° C. to effect the esterification of free alcohols and fatty acids contained in said wool fat;

(b) subjecting the resulting product of step (a) to intimate contact with a nonaqueous polar solvent at a temperature of at least 80° C. until it is essentially completely dissolved;

(c) cooling the product of step (b) to a temperature in the range of −20° to −30° C. to form a precipitated sediment;

(d) separating said precipitated sediment and dissolving it in a nonpolar organic solvent;

(e) flushing the resulting nonpolar organic solvent solution with water;

(f) separating water from the nonpolar organic solvent solution to provide a dehydrated product;

(g) subjecting the dehydrated nonpolar organic solvent solution to chromatographic purification; and (h) removing solvent from said chromatographically purified solution to produce said oil additives.

2. A method in accordance with claim 1 in which additional fatty acid in an amount up to about 1% of the wool fat is added to the wool fat during the initial elevated temperature esterification reaction.

* * * * *